US00PP19650P2

(12) United States Plant Patent
Cook et al.

(10) Patent No.: US PP19,650 P2
(45) Date of Patent: Jan. 20, 2009

(54) ***OZOTHAMNUS* PLANT NAMED '40-24'**

(50) Latin Name: *Ozothamnus diosmifolius*
Varietal Denomination: 40-24

(75) Inventors: Edward Graham Cook, Helidon (AU); Esther Ruth Cook, Helidon (AU)

(73) Assignee: Amerinova Properties LLC, Bonsall, CA (US)

( * ) Notice: Subject to any disclaimer, the term of this patent is extended or adjusted under 35 U.S.C. 154(b) by 85 days.

(21) Appl. No.: 11/800,797

(22) Filed: May 7, 2007

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—Kent L Bell
(74) *Attorney, Agent, or Firm*—C. A. Whealy

(57) ABSTRACT

A new and distinct cultivar of *Ozothamnus* plant named '40-24', characterized by its upright plant habit; vigorous growth habit; short internodes; dense and bushy habit; freely flowering habit; and inflorescences arranged in corymbs with pink-colored involucral bracts.

1 Drawing Sheet

Botanical designation: *Ozothamnus diosmifolius.*
Cultivar denomination: '40-24'.

BACKGROUND OF THE INVENTION

The present invention relates to a new and distinct cultivar of *Ozothamnus* plant, botanically known as *Ozothamnus diosmifolius,* and hereinafter referred to by the name '40-24'.

The new *Ozothamnus* is a naturally-occurring branch mutation of a proprietary selection of *Ozothamnus diosmifolius* identified as code number 1366, not patented. The new *Ozothamnus* was discovered and selected by the Inventors in a controlled environment in Helidon, Queensland, Australia in September, 1998.

Asexual reproduction of the new *Ozothamnus* by vegetative cuttings in a controlled environment in Helidon, Queensland, Australia since 1999, has shown that the unique features of this new *Ozothamnus* are stable and reproduced true to type in successive generations.

SUMMARY OF THE INVENTION

The cultivar 40-24 has not been observed under all possible environmental conditions. The phenotype may vary somewhat with variations in environment such as temperature and light intensity, without, however, any variance in genotype.

The following traits have been repeatedly observed and are determined to be the unique characteristics of '40-24'. These characteristics in combination distinguish '40-24' as a new and distinct cultivar of *Ozothamnus:*

1. Upright plant habit.
2. Vigorous growth habit.
3. Short internodes; dense and bushy habit.
4. Freely flowering habit.
5. Inflorescences arranged in corymbs with pink-colored involucral bracts.

Plants of the new *Ozothamnus* differ from plants of the parent selection in the following characteristics:

1. Plants of the new *Ozothamnus* are shorter than plants of the parent selection.
2. Plants of the new *Ozothamnus* flower earlier than plants of the parent selection.

Plants of the new *Ozothamnus* can be compared to plants of the *Ozothamnus* cultivar Just Blush, not patented. In side-by-side comparisons conducted in Helidon, Queensland, Australia, plants of the new *Ozothamnus* differed from plants of the cultivar Just Blush in the following characteristics:

1. Plants of the new *Ozothamnus* were more rounded than plants of the cultivar Just Blush.
2. Corymbs of plants of the new *Ozothamnus* were larger than corymbs of plants of the cultivar Just Blush.
3. Plants of the new *Ozothamnus* had darker pink-colored involucral bracts than plants of the cultivar Just Blush.

BRIEF DESCRIPTION OF THE PHOTOGRAPHS

The accompanying photographs illustrate the overall appearance of the new *Ozothamnus.* The photographs show the colors as true as it is reasonably possible to obtain in colored reproductions of this type. Colors in the photographs may differ slightly from the color values cited in the detailed botanical description which accurately describe the colors of the new *Ozothamnus.*

The photograph at the bottom of the sheet comprises a side perspective view of a typical flowering plant of '40-24' grown in a container.

The photograph at the top of the sheet is a close-up view of a typical corymb of '40-24'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Bonsall, Calif. during the autumn in an outdoor nursery and under conditions and practices which approximate those generally used in commercial *Ozothamnus* production. During the production of the plants, day temperatures ranged from about 18° C. to 38° C. and night temperatures ranged from 13° C. to 24° C. Measurements and numerical values represent averages for typical flowering plants. Plants were about five months old when the photographs and description were taken.

Botanical classification: *Ozothamnus diosmifolius* cultivar 40-24.

Parentage: Naturally-occurring branch mutation of a proprietary selection of *Ozothamnus diosmifolius* identified as code number 1366, not patented.

Propagation:

*Type.*—By vegetative cuttings.

*Time to initiate roots, summer.*—About two to three weeks.

*Time to produce a rooted young plant, summer.*—About six to eight weeks.

*Root description.*—Fine, fibrous; white in color.

Rooting habit.—Moderate branching; moderately dense.

Plant description:

Plant form/growth habit.—Upright plant habit; inverted triangle. Vigorous growth habit. Short internodes; dense and bushy habit. Freely branching habit with about five to six lateral branches per plant with numerous secondary and tertiary lateral branches.

Plant height.—About 72 cm.

Plant diameter or spread.—About 56 cm.

Lateral branches.—Length: About 57 cm. Diameter: About 6 mm. Internode length: About 5 cm. Aspect: Upright to somewhat outwardly spreading. Strength: Strong. Texture, developing: Pubescent. Texture, mature: Woody. Color, developing: 148B. Color, mature: 177A.

Foliage description:

*Arrangement.*—Alternate to whorled; simple; sessile.

*Length.*—About 1.2 cm.

*Width.*—About 1 mm.

*Shape.*—Acicular.

*Apex.*—Mucronate.

*Base.*—Attenuate, clasping.

*Margin.*—Entire.

*Texture, upper surface.*—Rough, granular.

*Texture, lower surface.*—Pubescent.

*Venation pattern.*—Single midvein.

*Color.*—Developing foliage, upper surface: 146A. Developing foliage, lower surface: 146B. Fully expanded foliage, upper surface: 147A; venation, 147A. Fully expanded foliage, lower surface: 147B; venation, 147B.

Inflorescence description:

*Appearance.*—Composite inflorescence form without ray florets; inflorescences arranged in terminal and axillary corymbs; corymbs hemispherical. Inflorescences face upright to outward. Freely flowering habit; about 42 inflorescences and inflorescence buds per corymb. Inflorescences persistent. Inflorescences not fragrant.

*Time to flower.*—Under mild weather conditions, plants will flower year-round in Southern California. Inflorescences last about three to four weeks on the plant.

*Inflorescence bud.*—Height: About 3 mm. Diameter: About 3 mm. Shape: Rounded. Color: 61B to 61C.

*Inflorescence size.*—Diameter: About 2.7 cm to 4.6 cm. Depth (height): About 3.8 cm. Disc diameter: About 3 mm. Receptacle diameter: About 4 mm. Receptacle height: About 4 mm to 5 mm.

*Ray florets.*—Ray floret development has not been observed.

*Disc florets.*—Shape: Tubular; apex dentate. Length: About 4 mm. Diameter: About 1 mm. Number of disc florets per inflorescence: About 35. Color, immature and mature: Apex: Close to 155A. Midsection and base: Close to 148C.

*Phyllaries.*—Quantity per inflorescence: About 30 arranged in about five to six whorls. Length: About 3 mm. Width: About 2 mm. Shape: Ovate. Apex: Acute. Base: Truncate. Margin: Entire. Texture, upper and lower surfaces: Smooth, glabrous. Color, immature, upper and lower surfaces: Close to 61C; towards the apex, close to 61B. Color, mature, upper surface: Close to 155D. Color, mature, lower surface: Close to 62C; with development, color becomes closer to 155D tinted with 62D.

*Peduncles.*—Length: About 1.3 cm to 1.7 cm. Diameter: About 1 mm. Strength: Strong. Aspect: Upright to about 45°. Texture: Pubescent. Color: Close to 148C.

*Reproductive organs.*—Androecium: Quantity per disc floret: Five. Anther shape: Lanceolate. Anther length: About 1.5 mm. Anther color: Close to 155A. Filament length: About 2 mm. Filament color: Close to 155A. Pollen amount: Scarce. Pollen color: Close to 155A. Gynoecium: Quantity per disc floret: One. Pistil length: About 3 mm. Stigma shape: Bi-parted. Stigma color: Close to 155A. Style length: About 1.5 mm. Style color: Close to 155A. Ovary color: Close to 148C.

*Seed/fruit.*—Seed and fruit development have not been observed.

Disease/pest resistance: Plants of the new *Ozothamnus* have not been shown to be resistant to pathogens and pests common to *Ozothamnus*.

Garden performance: Plants of the new *Ozothamnus* have exhibited good tolerance to rain and wind and have been observed to tolerate temperatures from about −5° C. to about 40° C.

It is claimed:

1. A new and distinct *Ozothamnus* plant named '40-24' as illustrated and described.

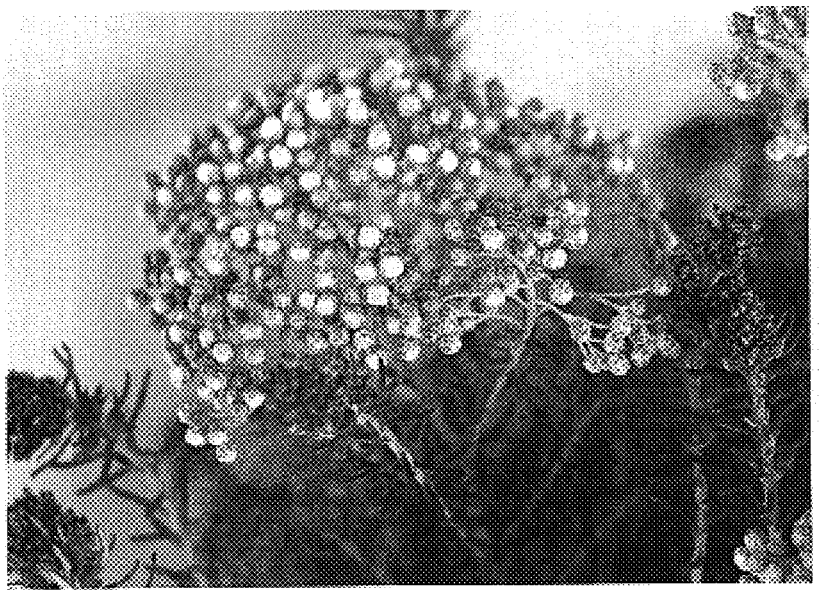
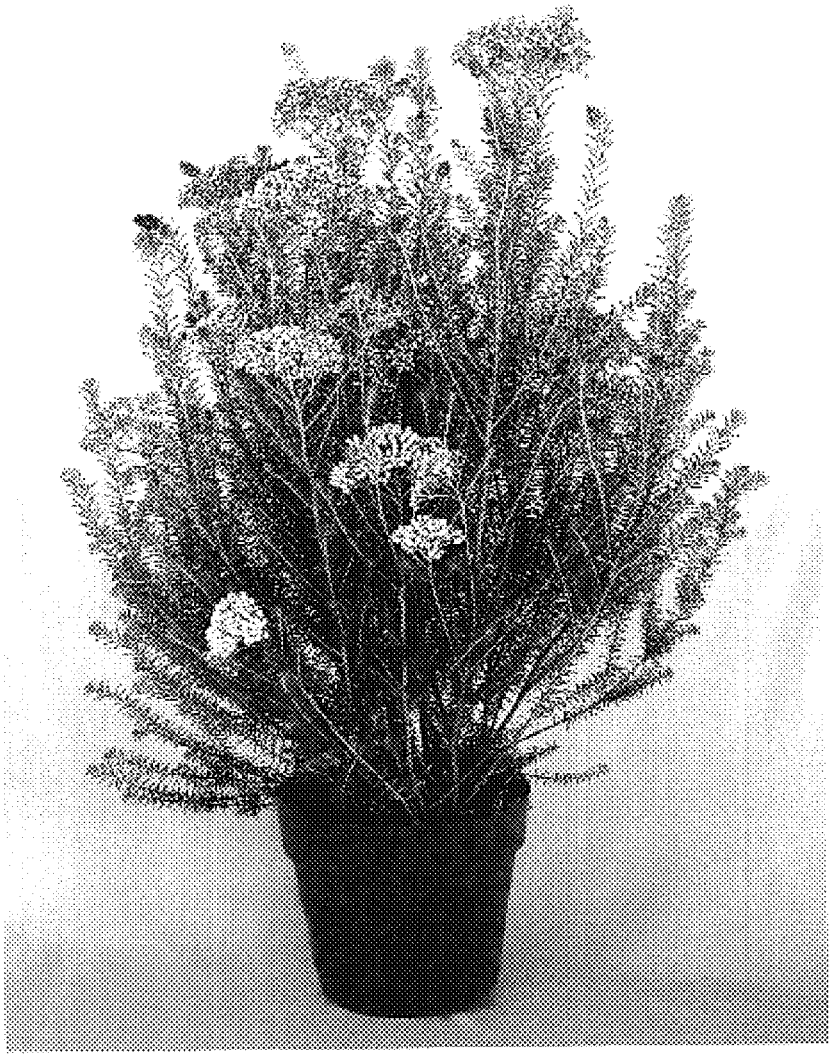

* * * * *